(12) United States Patent
Giddings et al.

(10) Patent No.: US 9,999,356 B2
(45) Date of Patent: *Jun. 19, 2018

(54) STRAIN SENSOR ELEMENT AND BLOOD PRESSURE SENSOR

(71) Applicant: Kabushiki Kaisha Toshiba, Minato-ku (JP)

(72) Inventors: Alexander Devin Giddings, Kanagawa-ken (JP); Hideaki Fukuzawa, Kanagawa-ken (JP); Yoshihiko Fuji, Kanagawa-ken (JP); Hiromi Yuasa, Kanagawa-ken (JP); Michiko Hara, Kanagawa-ken (JP); Shuichi Murakami, Tokyo (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 267 days.

This patent is subject to a terminal disclaimer.

(21) Appl. No.: 14/813,783

(22) Filed: Jul. 30, 2015

(65) Prior Publication Data

US 2015/0338292 A1 Nov. 26, 2015

Related U.S. Application Data

(63) Continuation of application No. 14/219,860, filed on Mar. 19, 2014, now Pat. No. 9,131,856, which is a
(Continued)

(30) Foreign Application Priority Data

Sep. 30, 2010 (JP) ................. 2010-223175

(51) Int. Cl.
*A61B 5/021* (2006.01)
*G01B 7/24* (2006.01)
*G01L 1/12* (2006.01)

(52) U.S. Cl.
CPC .......... *A61B 5/021* (2013.01); *A61B 5/02108* (2013.01); *G01B 7/24* (2013.01); *G01L 1/125* (2013.01)

(58) Field of Classification Search
CPC .................. G01L 1/00; G01B 7/24
See application file for complete search history.

(56) References Cited

U.S. PATENT DOCUMENTS

| 5,168,760 A | 12/1992 | Wun-Fogle et al. |
| 5,585,986 A | 12/1996 | Parkin |

(Continued)

FOREIGN PATENT DOCUMENTS

| JP | 2002-148132 | 5/2002 |
| JP | 2002-357488 | 12/2002 |

(Continued)

OTHER PUBLICATIONS

U.S. Appl. No. 13/927,886, filed Jun. 26, 2013, 2014-0090486, Fuji et al.

(Continued)

*Primary Examiner* — Harshad R Patel
*Assistant Examiner* — Jamel Williams
(74) *Attorney, Agent, or Firm* — Oblon, McClelland, Maier & Neustadt, L.L.P.

(57) ABSTRACT

A strain sensor element comprises a laminated film which has a magnetic free layer, a spacer layer, and a magnetic reference layer. The free layer has a variable magnetization direction and a out-of-plane magnetization direction. The reference layer has a variable magnetization direction which is pinned more strongly than the magnetization of the free layer. The spacer layer provided between the free layer and the reference layer. A pair of electrodes is provided with a plane of the laminated film. A substrate is provided with either of the pair electrodes and can be strained. The rotation
(Continued)

10 : Strain sensor element
15 : Substrate
20 : Reference layer
30 : Spacer layer
40 : Free layer
50 : Magnetoresistance (MR) element (spin-valve film)
70: Under-layer ( comprising buffer layer, seed layer, and coating layer or like)

angle of the magnetization of the free layer is different from the rotation angle of the magnetization of the reference layer when the substrate is distorted. Electrical resistance is changed depending on the magnetization angle between the free layer and the reference layer, which allows the element to operate as a strain sensor.

21 Claims, 22 Drawing Sheets

Related U.S. Application Data continuation of application No. 13/110,392, filed on May 18, 2011, now Pat. No. 8,760,154.

(56) References Cited

U.S. PATENT DOCUMENTS

| | | | | |
|---|---|---|---|---|
| 5,686,837 | A | 11/1997 | Coehoorn et al. | |
| 6,694,822 | B1 | 2/2004 | Ganapathi et al. | |
| 6,988,414 | B2* | 1/2006 | Ruhrig | G01L 1/125 324/207.21 |
| 7,732,881 | B2* | 6/2010 | Wang | G11C 11/15 257/295 |
| 8,760,154 | B2* | 6/2014 | Giddings | G01B 7/24 324/209 |
| 8,933,909 | B2 | 1/2015 | Giddings et al. | |
| 8,958,574 | B2 | 2/2015 | Fukuzawa et al. | |
| 8,973,446 | B2 | 3/2015 | Fukuzawa et al. | |
| 9,032,808 | B2 | 5/2015 | Giddings et al. | |
| 9,046,549 | B2 | 6/2015 | Higashi et al. | |
| 2004/0050172 | A1 | 3/2004 | Quandt et al. | |
| 2004/0154405 | A1 | 8/2004 | Ganapathi et al. | |
| 2007/0139827 | A1 | 6/2007 | Gao et al. | |
| 2012/0245477 | A1 | 9/2012 | Giddings et al. | |
| 2013/0076687 | A1 | 3/2013 | Giddings et al. | |
| 2013/0170669 | A1 | 7/2013 | Fukuzawa et al. | |
| 2013/0255069 | A1 | 10/2013 | Higashi et al. | |
| 2013/0255393 | A1 | 10/2013 | Fukuzawa et al. | |
| 2014/0090486 | A1 | 4/2014 | Fuji et al. | |
| 2014/0137658 | A1 | 5/2014 | Higashi et al. | |
| 2014/0137668 | A1 | 5/2014 | Fukuzawa et al. | |

FOREIGN PATENT DOCUMENTS

| | | |
|---|---|---|
| JP | 2002-357489 | 12/2002 |
| JP | 2003-294545 | 10/2003 |
| JP | 2008-107323 | 5/2008 |
| JP | 2009-194393 | 8/2009 |

OTHER PUBLICATIONS

U.S. Appl. No. 14/045,153, filed Oct. 3, 2013, 2014-0137658, Higashi et al.
U.S. Appl. No. 14/047,108, filed Oct. 7, 2013, 2014-0137668, Fukuzawa et al.
Japanese Office Action dated Oct. 2, 2012, in Japan Patent Application No. 2010-223175 (with English translation).

* cited by examiner

[Fig.1A]
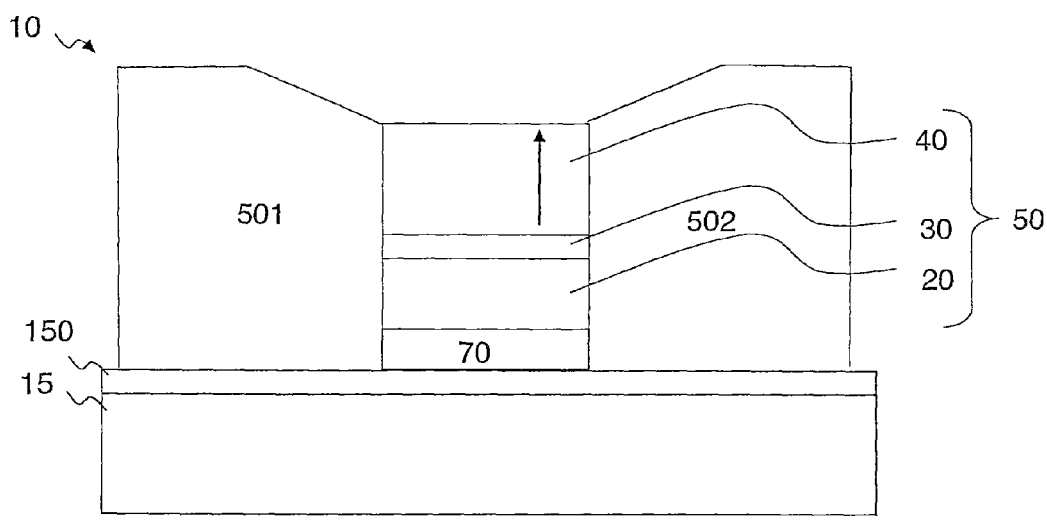
10 : Strain sensor element
15 : Substrate
20 : Reference layer
30 : Spacer layer
40 : Free layer
50 : Magnetoresistance (MR) element (spin-valve film)
70: Under-layer ( comprising buffer layer, seed layer, and coating layer or like)

[Fig.1B]
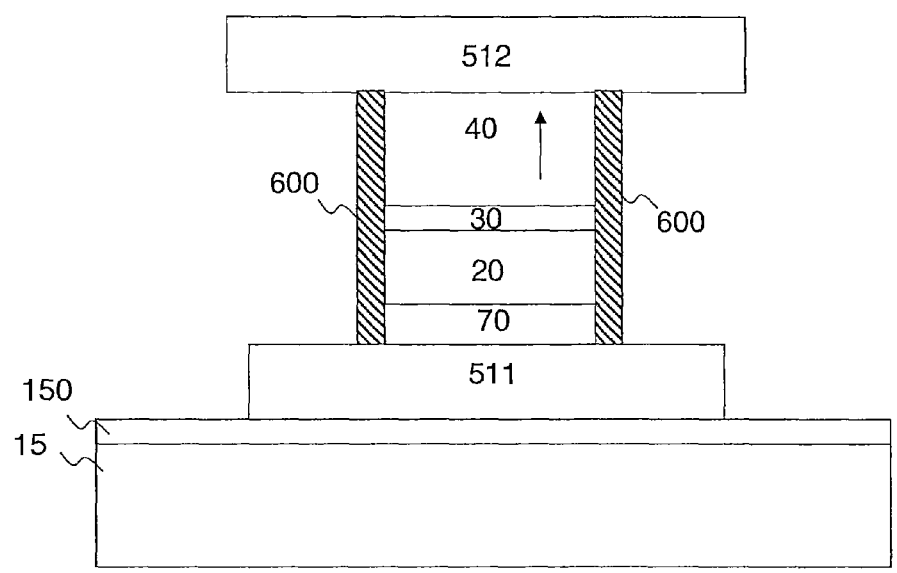

[Fig.1C]
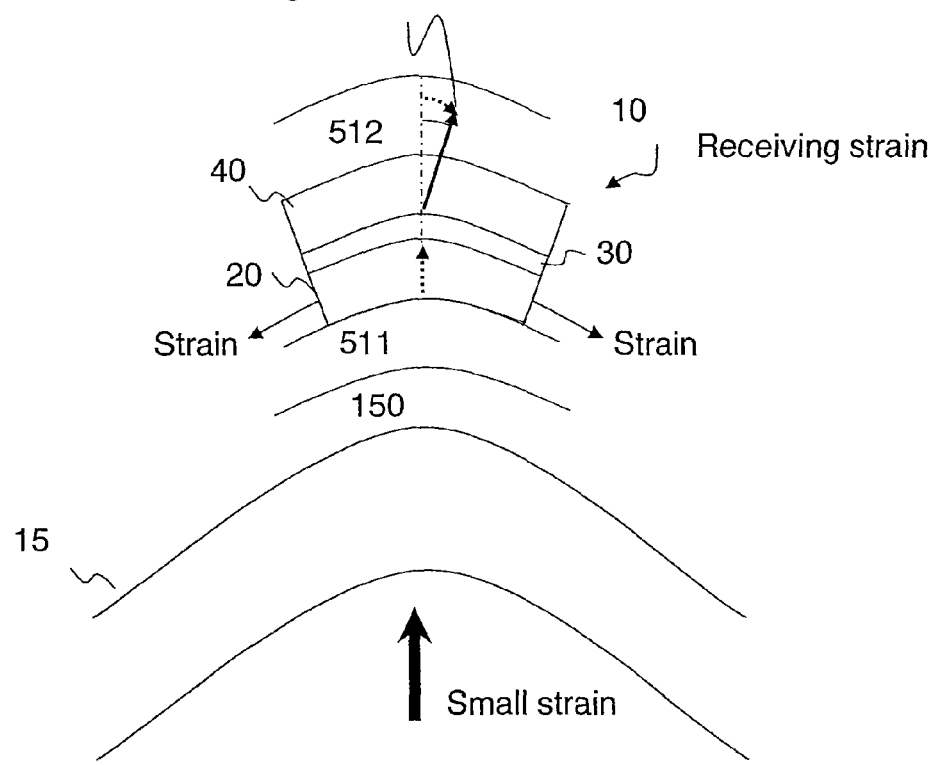

[Fig.1D]
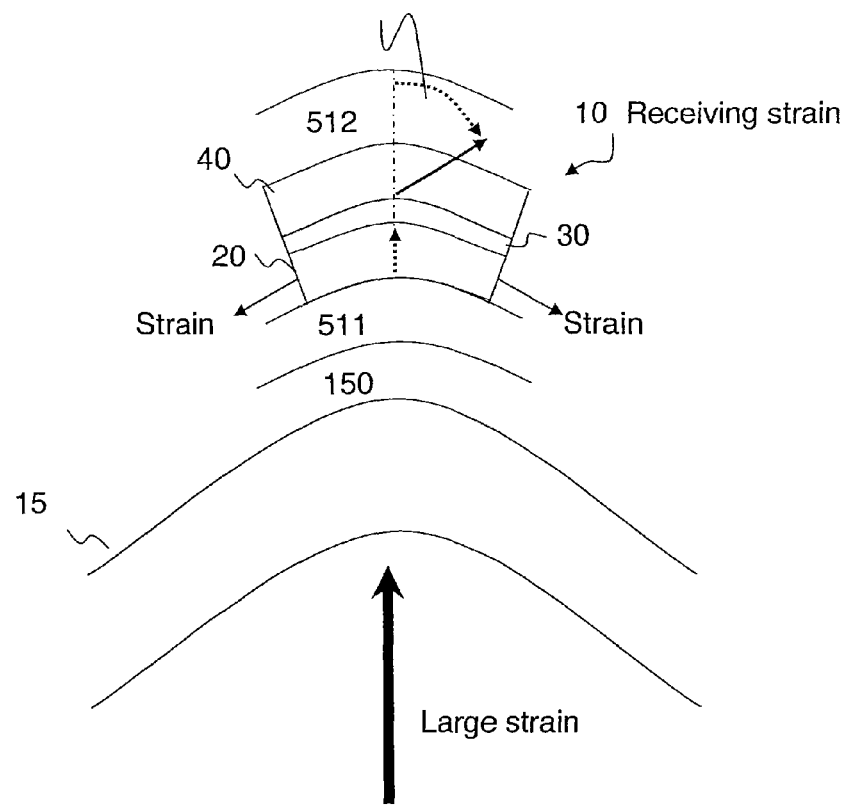

[Fig.2A]
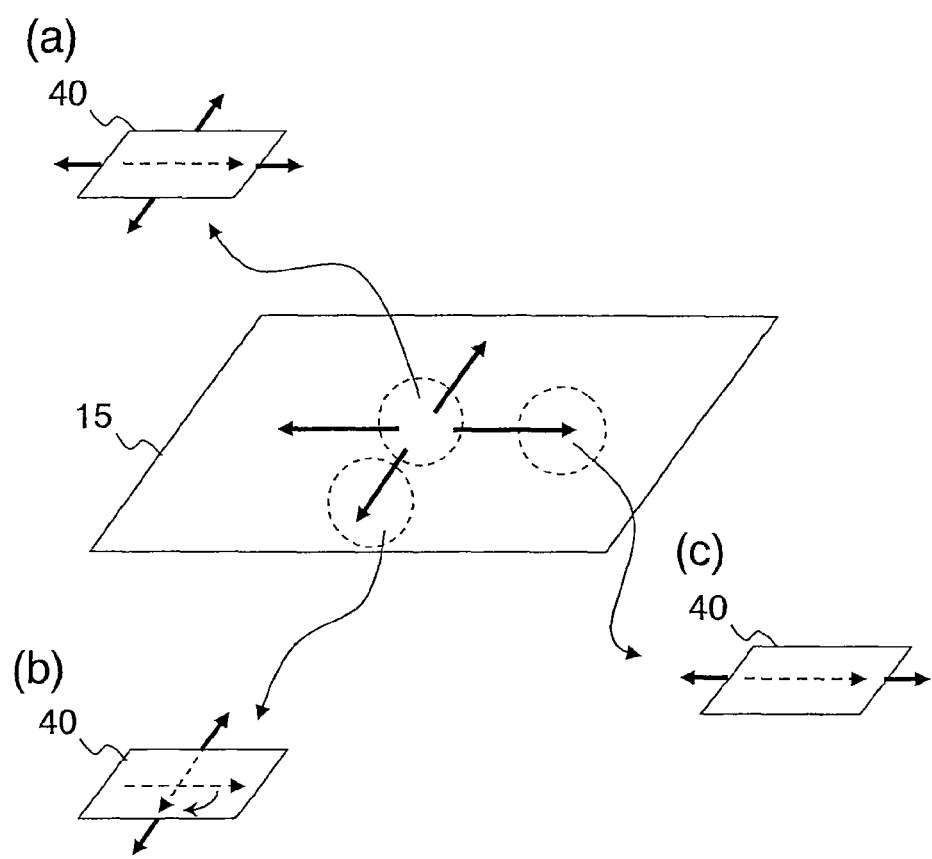

[Fig.2B]
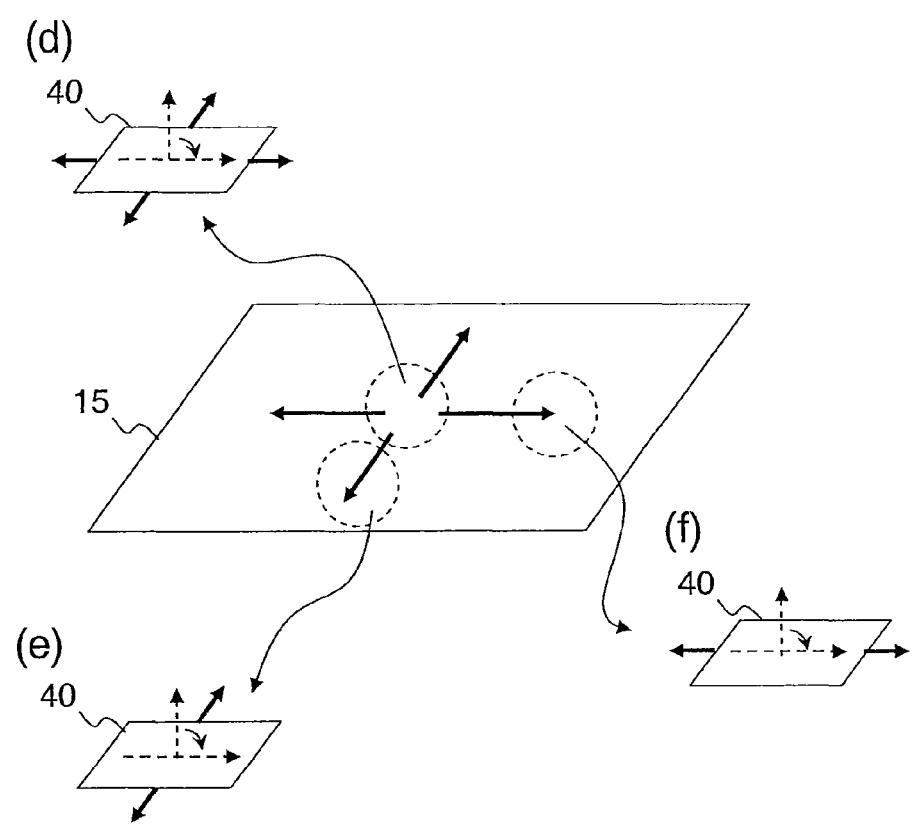

[Fig.3]
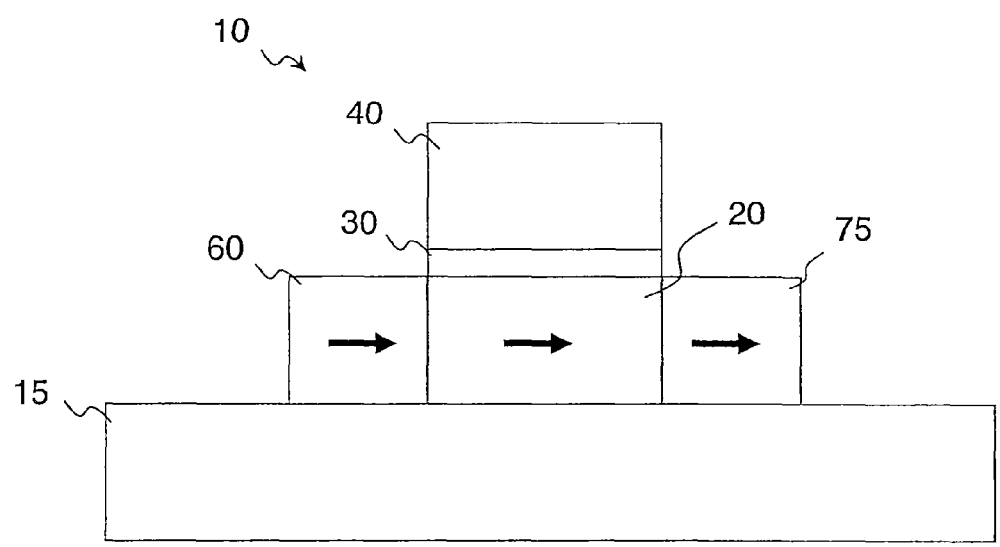
60, 75 : Ferromagnetic layer

[Fig.4]
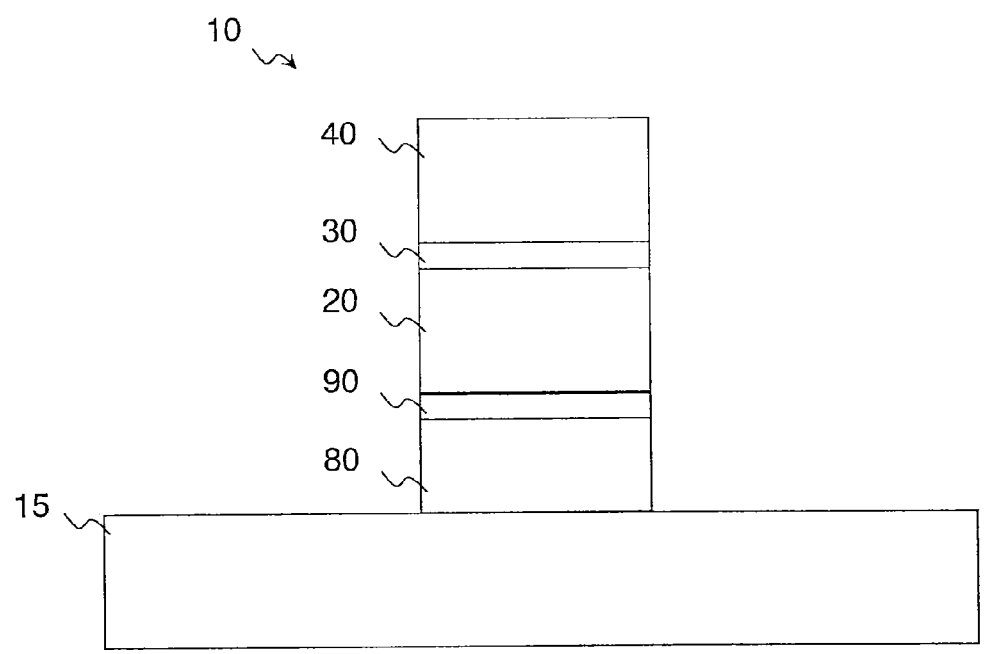
80 : Ferromagnetic layer
90 : Nonmagnetic layer

[Fig.5]
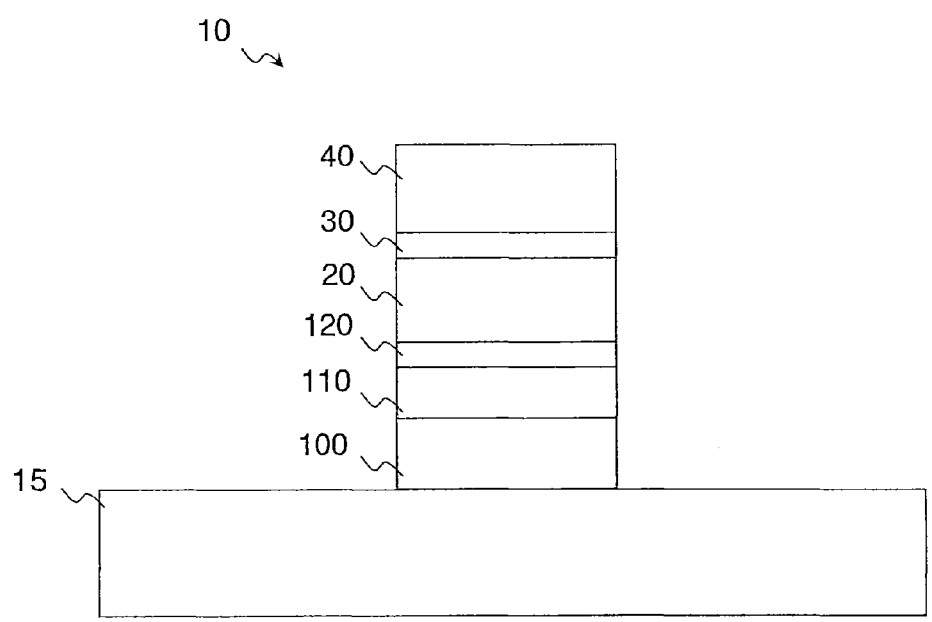
100 : Antiferromagnetic layer
110 : Ferromagnetic layer
120 : Nonmagnetic layer

[Fig.6]
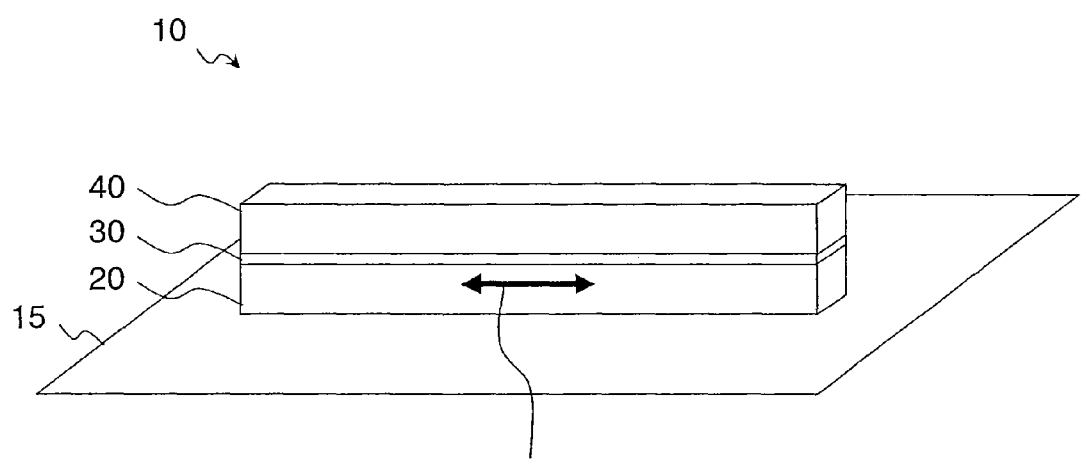
The direction of the magnetization is longitudinal.

[Fig.7]
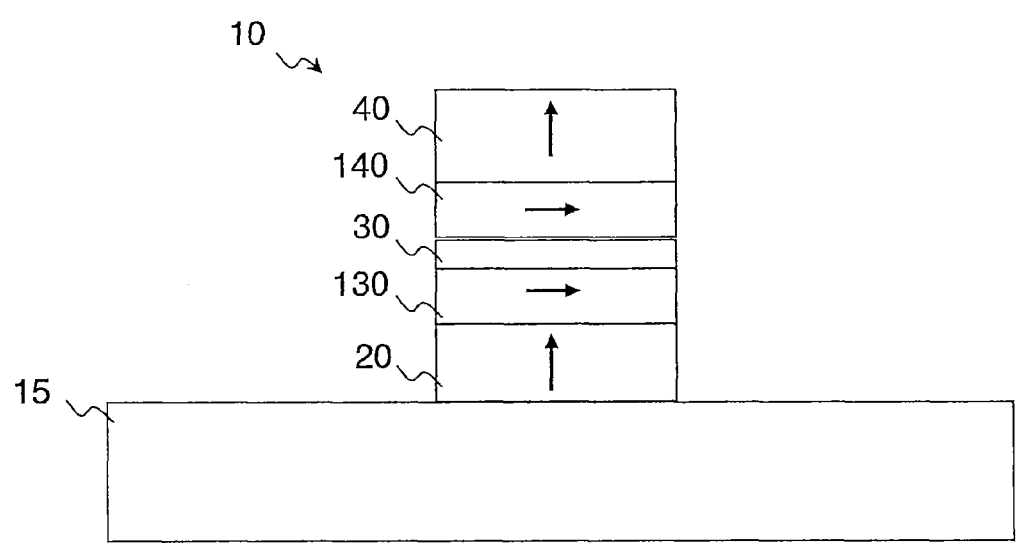
130, 140 : Ferromagnetic layer

[Fig.8]
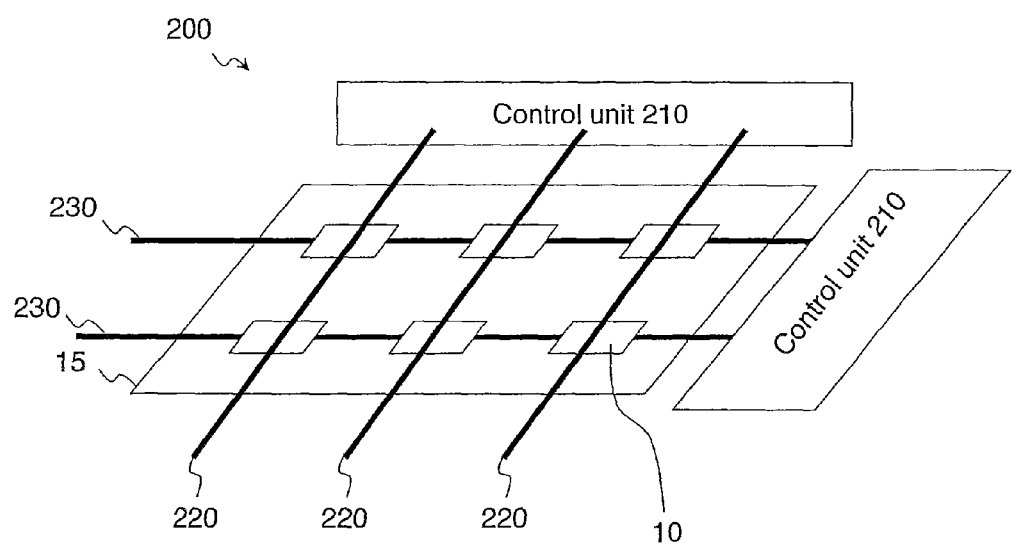
200 : Device
210 : Control unit
220 : word line
230 : Bit line

[Fig.9]
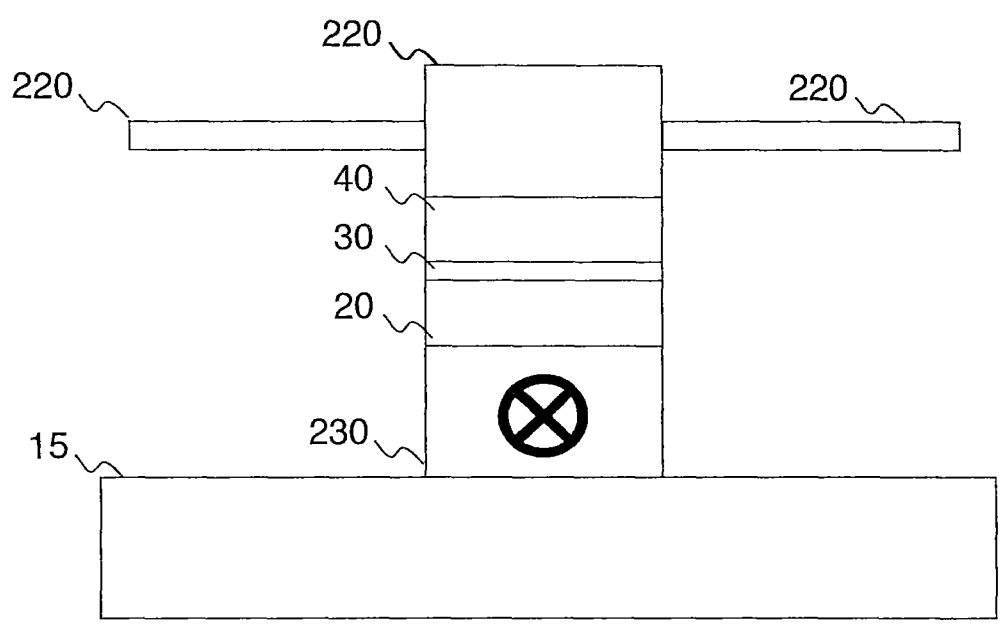

[Fig.10]
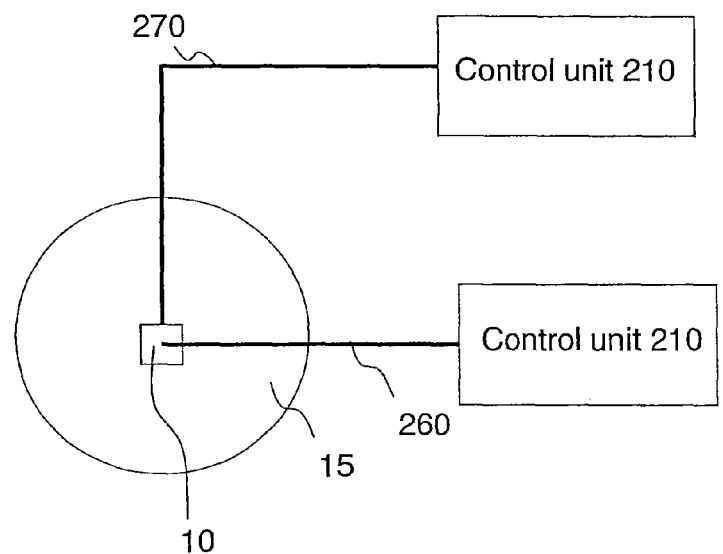
260, 270 : electrode

[Fig.11A]
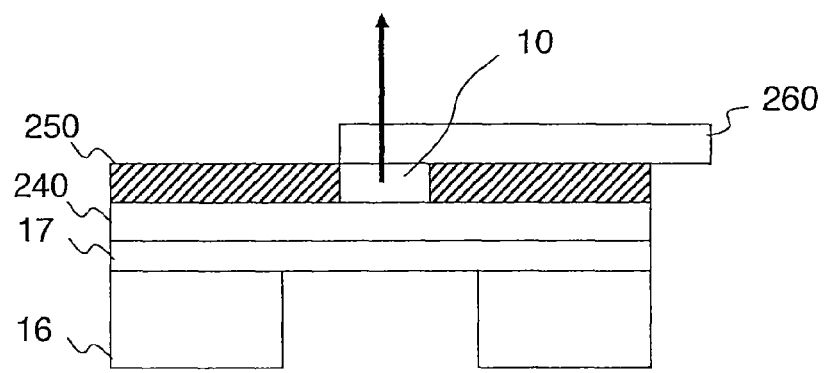
240 : conductive film
250 : insulating layer

[Fig.11B]
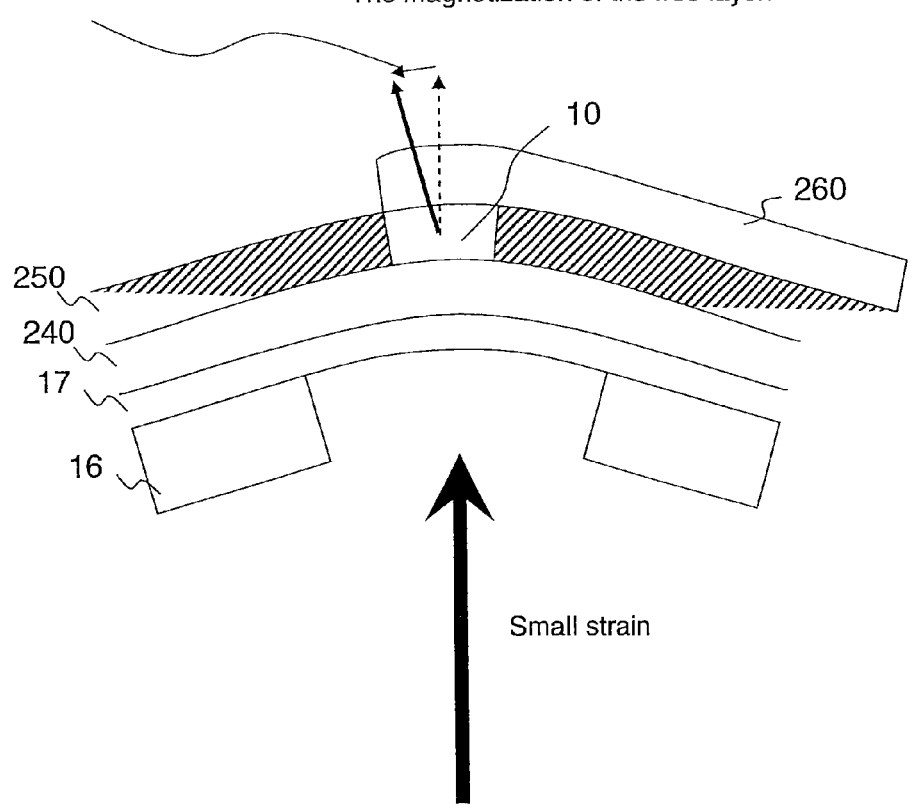

[Fig.11C]
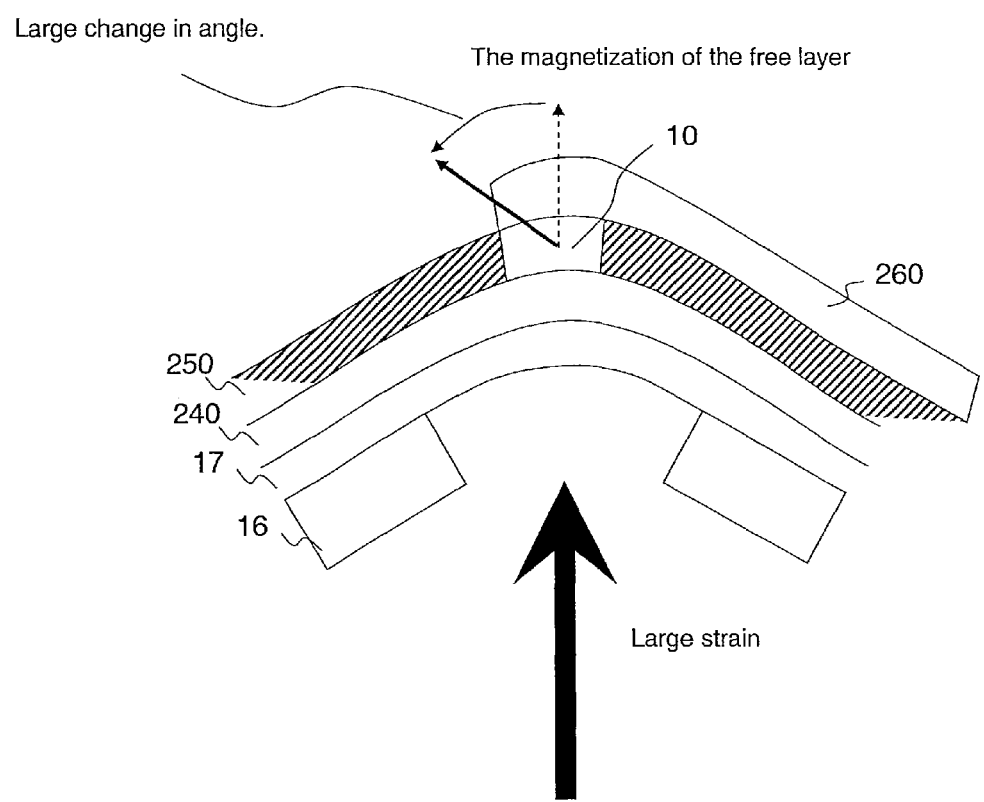

[Fig.12]
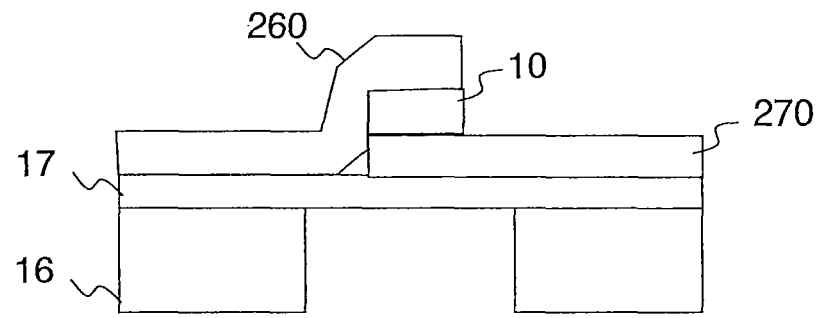

[Fig.13]
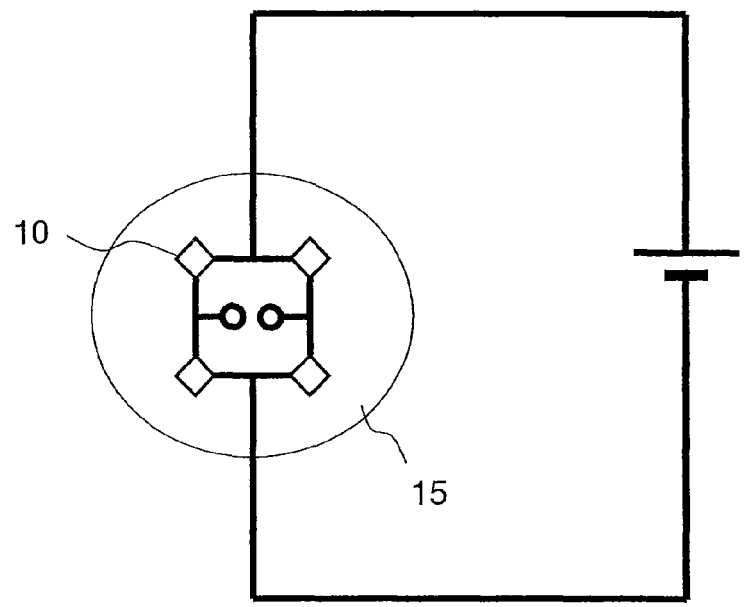

[Fig.14]
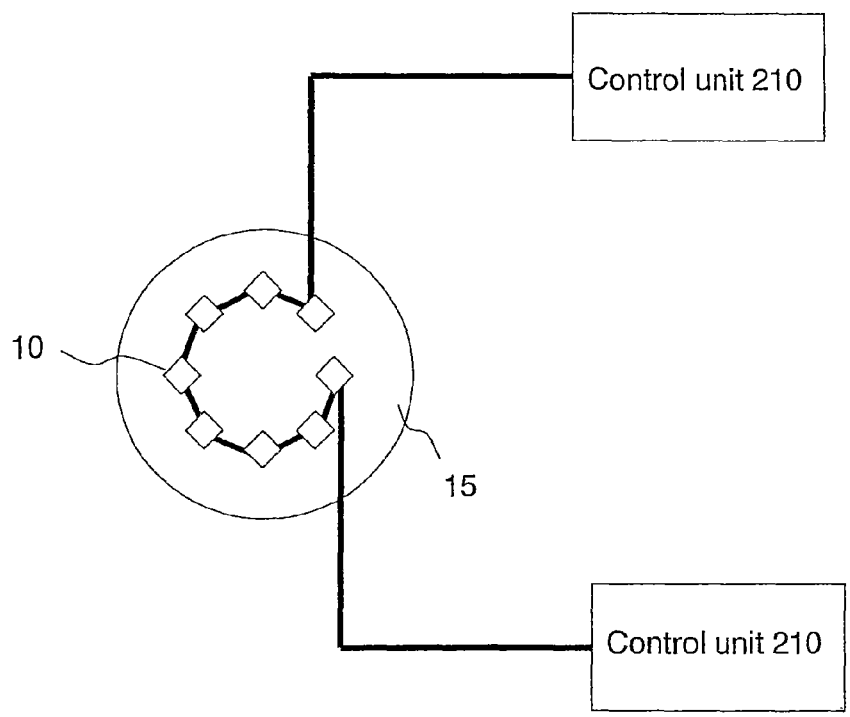

[Fig.15]
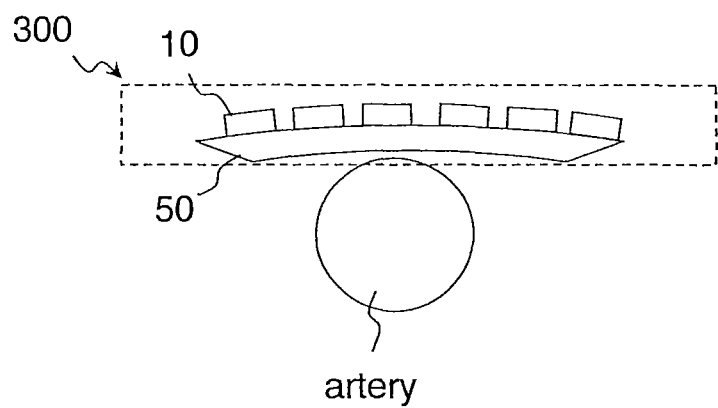
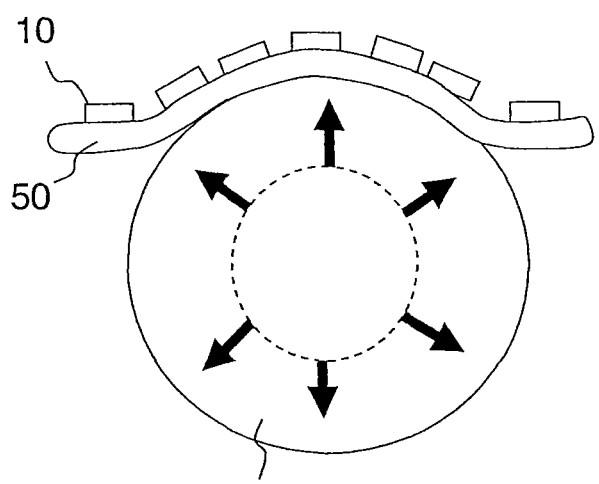
The artery is expanded by pulse.

[Fig.16]
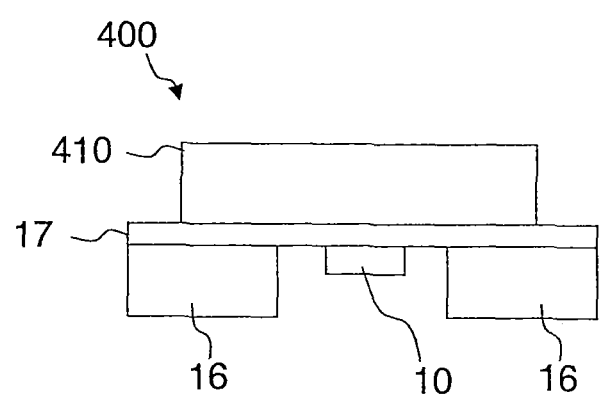
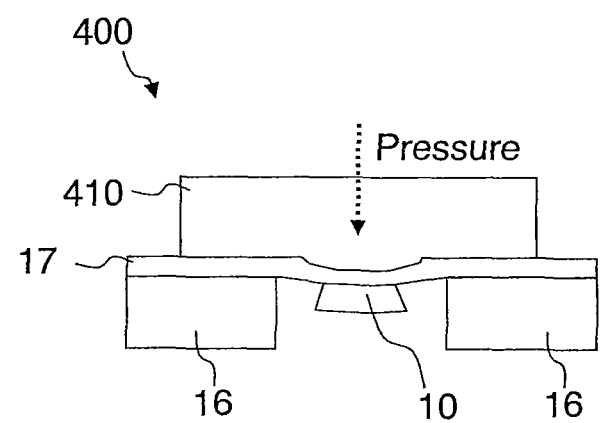

STRAIN SENSOR ELEMENT AND BLOOD PRESSURE SENSOR

CROSS REFERENCE TO RELATED APPLICATION

This application is a continuation of U.S. application Ser. No. 14/219,860 filed Mar. 19, 2014, which is a continuation of U.S. application Ser. No. 13/110,392 filed May 18, 2011, and is based upon and claims the benefit of priority from the prior Japanese Patent Application No. JP2010-223175, filed on Sep. 30, 2010 the entire contents of each of which are incorporated herein by reference.

FIELD

Embodiments described herein relate to a strain sensor, a pressure sensor element, and a blood pressure sensor.

BACKGROUND

A spin-valve film comprises thin magnetic layers which are laminated.

Resistance of the spin-valve film is changed by an external magnetic field. This change is known as MR (magnetoresitive) effect. The MR effect is caused by various physical effects. GMR (giant magnetoresistive) effect and TMR (tunneling magnetoresistive) effect are well known.

The spin-valve film is comprised of two or more ferromagnetic layers separated by a spacer layer. The magnetoresistance is determined by the relative orientations of magnetization of adjacent ferromagnetic layers. When two ferromagnetic layers have magnetizations with a parallel alignment the spin-valve film can be in a low resistance state. When the two magnetizations have an anti-parallel alignment the spin-valve film can be in a high resistance state. When angles of magnetizations in the adjacent ferromagnetic layers are at intermediate angles the spin-valve film can be in an intermediate resistance state.

In one of at least two ferromagnetic layers, a magnetic layer whose magnetization is easily variable is known as a free layer. A magnetic layer whose magnetization is not easily variable is known as a reference layer.

By using the magnetoresistance phenomenon, whereby the resistance of the spin-valve film is changed via an external magnetic field, the spin-valve film is used as a magnetic field sensor element. As a result of their good magnetic field sensitivity, the spin-valve film has widely been used in the read-head of HDDs (hard disk drives). Additionally, spin-valve films are used as part of the memory cell of MRAM (magnetic random access memory).

The spin-valve film can detect not only an external magnetic field, but also an external strain. This phenomenon enables us to use the spin-valve film as a strain sensor element or a pressure sensor element. The physical origin for the change in magnetization of a ferromagnetic layer by strain is an inverse-magnetostrictive effect. A brief explanation of this effect as follows.

The magnetostrictive effect is a phenomenon where a magnetic material's shape changes when the magnetization of the magnetic material is changed. The extent of the shape change of the magnetic material is determined by the magnitude of the magnetization and the direction of the magnetization. Therefore, the shape change is controlled by the magnitude of the magnetization and the direction of the magnetization. The amount of change which can occur from the magnetostriction of the magnetic material is described by the magnetostrictive coefficient $\lambda$. The magnetostrictive coefficient $\lambda$ depends on the composition of the magnetic material and the layer structure of the magnetic material.

A phenomenon complementary to the magnetostrictive effect, the inverse-magnetostrictive effect, is also known. With the inverse-magnetostrictive effect, the magnetization of a magnetic material can be changed when the magnetic material is stressed, for example by the application of an external strain. The magnitude of the change in magnetization depends on the magnitude of an external strain and the magnetostrictive coefficient of the magnetic material. The magnetostrictive coefficient relating to the inverse-magnetostrictive effect is same as the magnetostrictive coefficient $\lambda$ from the magnetostrictive effect because the magnetostrictive effect is converse to the inverse-magnetostrictive effect.

The magnetostrictive effect and the inverse-magnetostrictive effect may have a positive magnetostrictive coefficient or a negative magnetostrictive coefficient. The magnitude and sign of these coefficients depend on the composition of the magnetic material and the layer structure of the magnetic material.

If the magnetic material has a positive magnetostrictive coefficient, the direction of the magnetization of the magnetic material is aligned in the direction of a tensile stress or away from a compressive stress.

On the other hand, in the case of the negative magnetostrictive coefficient, the action is opposite to the case of the positive magnetostrictive coefficient. Thus, the direction of the magnetization of the magnetic material is changes to align towards a compressive stress or away from a tensile stress.

The inverse-magnetostrictive effect can be used to change the direction of the magnetization of the free layer in the spin-valve film. When an external strain is applied to the spin-valve film, an angular difference between the magnetization of the reference layer and the magnetization of the free layer is generated. This angular difference causes the resistance of the spin-valve film to change through the MR effect. Thus, the spin-valve film can be used as the basis of the strain sensor element.

BRIEF DESCRIPTION OF THE DRAWINGS

Aspects of this disclosure can become apparent upon reading the following detailed description and upon reference to the accompanying drawings. The description and the associated drawings are provided to illustrate embodiments of the invention and not limited to the scope of the invention.

FIG. 1A is a view showing a strain sensor element according to a first embodiment.

FIG. 1B is a view showing a strain sensor element according to a first embodiment.

FIG. 1C is a view showing a strain sensor element according to a first embodiment.

FIG. 1D is a view showing a strain sensor element according to a first embodiment.

FIG. 2A is a view showing a modified first example of the first embodiment.

FIG. 2B is a view showing a modified first example of the first embodiment.

FIG. 3 is a view showing a modified first example of the first embodiment.

FIG. 4 is a view showing a modified second example of the first embodiment.

FIG. 5 is a view showing a modified third example of the first embodiment.

FIG. 6 is a view showing a modified fourth example of the first embodiment.

FIG. 7 is a view showing a modified fifth example of the first embodiment.

FIG. 8 is a view showing a pressure sensor device according to a second embodiment.

FIG. 9 is a view showing a strain sensor device according to a second embodiment.

FIG. 10 is a view showing a strain sensor device according to a second embodiment.

FIG. 11A is a view showing a strain sensor device according to a second embodiment.

FIG. 11B is a view showing a strain sensor device according to a second embodiment.

FIG. 11C is a view showing a strain sensor device according to a second embodiment.

FIG. 12 is a view showing a strain sensor device according to a second embodiment.

FIG. 13 is a view showing a strain sensor device according to a second embodiment.

FIG. 14 is a view showing a strain sensor device according to a second embodiment.

FIG. 15 is a view showing a strain sensor apparatus according to a third embodiment.

FIG. 16 is a view showing a strain sensor apparatus according to a third embodiment.

DETAILED DESCRIPTION

Embodiments can be described below with reference to drawings. Wherever possible, the same reference numerals or marks can be used to denote the same or like portions throughout figures, and overlapped explanations are omitted in embodiments following a first embodiment.

As the embodiments of the invention, there are two types of embodiments. The first is a strain sensor element, and the second is a pressure sensor element. The strain sensor element is an element detecting a compressive strain and a tensile strain of a substrate. As shown in FIG. 1, the strain sensor element works if a spin-valve film is formed on the substrate. The pressure sensor element, mentioned as the second embodiment, is an element comprising a membrane where the strain sensor is formed on the membrane. The membrane works such as a diaphragm. Thus, the pressure sensor element comprises the strain sensor element. The embodiment of the invention is effective both for the strain sensor element and the pressure sensor element because the embodiment of the invention relates to the spin-valve film of the strain sensor element.

The pressure sensor element is, moreover, classified into two groups. The first classification is the pressure sensor element which comprises of a conventional substrate material, such as Si or similar materials, with a membrane. The second classification is the pressure sensor element which does not use a membrane and comprises a substrate made of a material which is flexible. The embodiment of the invention is effective both for the element structure using the membrane and for the element structure without a membrane but made with a flexible material.

A substrate such as Si or a membrane can be used for the pressure sensor element. The flexible material also can be used for the substrate.

The membrane functions in order to transform an external stress. When the external stress applies to the membrane from outside, various magnitudes of strain are generated, depending on the layout of the membrane and a position of the membrane. The strain, which varies over the area of the membrane, can be detected by placing the strain sensor element on many positions of the membrane. The pressure sensor element will be effective if the spin-valve element is positioned on the membrane where it can detect the resultant strain FIG. 1A and FIG. 1B show a strain sensor element 10. The strain sensor element 10 has a spin-valve film comprising a spacer layer 30 and a free layer 40, formed on a substrate 15. A reference layer 20 and the free layer 40 are formed of a magnetic material. The spacer layer 30 is comprised of a nonmagnetic material. But, as mentioned below, the magnetic material can be used as the spacer layer 30. A pair of electrodes is used to supply an electric current to the spin-valve film. In a CIP (current in-plane) arrangement, a pair of electrodes, 501 and 502, is used, as shown in FIG. 1A. In a CPP (current perpendicular-to-plane) arrangement, a pair of electrodes, 511 and 512, is used, as shown in FIG. 1B. A priming layer 150 is used both of the CIP arrangement and the CPP arrangement in order to insulate the spin-valve film from the substrate 15 and to smooth any roughness in the surface of the substrate 15. An under-layer 70 is used as a base layer for the laminated film of the reference layer 20, the spacer layer 30, and the free layer 40. Each part of the laminated film is explained in detail. The laminated film is defined in the reference layer 20, the spacer layer 30, and the free layer 40.

The reference layer 20 is to be a "reference" for the magnetization of the free layer 40. To provide a reference for the magnetization of the free layer 40, the magnetization state of the reference layer 20 may be different to the state of the free layer 40. One of the embodiments is that the magnetization of the reference layer 20 is pinned so is independent of the external stress. In the cases where the reference layer 20 has in-plane magnetization, a pinning layer (mentioned below) such as IrMn or PtMn can be used under the reference layer 20. Instead of a simple pinning structure like this, a synthetic antiferromagnetic structure, comprising reference layer 20/Ru 0.9 nm/magnetic layer/the pinning layer/, can be used. If the reference layer 20 is a hard magnetic film with large magnetic anisotropy and this anisotropy energy is large enough compared to magnetostrictive energy of the reference layer 20, the magnetization of the reference layer 20 is not changed by the external stress. In this case, the pinning layer can be omitted.

The magnetization of the reference layer 20 does not need to be pinned when the external strain is applied to the reference layer 20. This is because the spin-valve film can detect the external strain as long as a relative magnetization angle exists between the reference layer 20 and the free layer 40 which can be changed by the external strain. The reference layer 20 comprises at least one element of Fe, Co, or Ni because the reference layer 20 is formed of a magnetic material.

The spacer layer 30 has some variations, depending on the physical origin of the MR effect. In the cases where the TMR effect causes the MR effect, MgO is often used as the spacer layer 30. The spacer layer 30 can also be formed of an oxide, a nitride, or an oxynitride, based on Al, Ti, Zn, Si, Hf, Ta, Mo, Wo, Nb, Cr, Mg, or Zr. In the cases where the GMR effect is the origin of the MR effect, the spacer layer 30 can be formed from a metal material such as Cu, Au, Ag, Al, or Cr, and these elements can be used in the CIP arrangement or the CPP arrangement. In addition to the metal layer like this being used, a CCP (current-confined-path) spacer can be also used for a CPP arrangement. The CCP spacer is formed from a nano-scaled metal paths, forming conductive channels through an insulating layer. The merit of using the CCP spacer is enhancing the MR effect and being able to control the magnitude of the resistance. A material for the metal paths of the CCP spacer is a material from the same group as same as the metal spacer, such as Cu, Au, Ag, Al, or Cr, or similar. The insulating layer of the CCP spacer is an oxide, a nitride, or an oxynitride, based on Al, Ti, Zn, Si, Hf, Ta, Mo, Wo, Nb, Cr, Mg, or Zr.

The feature of the free layer 40 in the invention being different from the conventional is that the direction of the magnetization of the free layer 40 is follows a perpendicular-anisotropy when the external strain is not applied. The perpendicular-anisotropy is defined that the direction of the magnetization is substantially perpendicular to the plane of the magnetic layer. On the other hand, an in-plane-anisotropy is defined that the direction of the magnetization is substantially parallel to the plane of the magnetic layer. In this specification, the perpendicular-anisotropy and the in-plane-anisotropy are defined as mentioned above. These states are shown in FIG. 1A and FIG. 1B. In these figures the direction of the magnetization is represented by an upward arrow, but downward arrow also can be used.

It has been also studied to use a magnetic layer with the perpendicular-anisotropy, for a MRAM (magnetic random access memory) or a STO (spin torque oscillator). The merit of using a perpendicular-anisotropy is different from the case of the MRAM and the STO and in the invention. In the case of the MRAM, the perpendicular-anisotropy is used in order to achieve a high density memory cell. In the case of the high density memory cell, it is necessary to stabilize the direction of a magnetization robustly so that scaling issues do not occur as the cell size is reduced. In the case of the in-plane-anisotropy, it is hard to realize the high density memory cell because the demagnetization field becomes larger with reduced size, which results in an unstable magnetization. Thus, scaling becomes hard to realize. Therefore the perpendicular-anisotropy is considered for archiving the high density memory cell, improving possibilities for scaling. This situation is same as the reason that PMR (perpendicular magnetic recording) in a magnetic recording media has already been realized for modern-era HDDs.

In the STO, a film structure which uses the perpendicular-anisotropy has been also studied. The reason is that it is beneficial to use a stable magnetization because good oscillation properties cannot be obtained without miniaturizing the size of the STO. The perpendicular-anisotropy for a miniaturized STO is a way to achieve this. Thus, it is advantageous to use the perpendicular-anisotropy for the miniaturized STO for the same reason as in the case of MRAM, though the scaling rule between the two cases is different. A second benefit for the STO is that a material with the perpendicular-anisotropy has a larger magnetic anisotropy. This is advantageous because using a material with the perpendicular-anisotropy can result in improved oscillating frequency of the STO by having the large magnetic anisotropy.

Compared to the above discussion, the purpose of using the perpendicular-anisotropy for the strain sensor element and the pressure sensor element in the embodiment of the invention is different from that of the use in the MRAM and the STO cases, described above. As mentioned before, a strain which is created in the strain sensor element in the membrane varies by location on the membrane. The relationship between strain and position on the membrane is complicated. The polarity difference when either a compressive strain or a tensile strain is generated will be depending on the location of the strain sensor element on the membrane.

Each strain sensor can detect either a compressive or a tensile strain depending on the easy axis of free layer and the polarity of magnetostriction. For example, a particular strain sensor can detect the strain as the resistance changes due to the change of magnetization of free layer under compressive strain, but the same sensor element cannot detect tensile strain because such strain cannot change the magnetization direction of free layer from the initial state. In order to detect a tensile strain, we need to use a free layer with the opposite polarity of magnetostriction to the previous sensor which can detect the compressive strain. Another option is that we need to use strain sensor having magnetic easy axis perpendicular to the previous sensor which can detect compressive strain. For both cases, such a realization is not used because it requires a double processing sequence. It also results in a worse SNR (signal-to-noise ratio) of the sensor element because only a part of the sensor can be used for the detection of strain.

On the other hand, by using the perpendicular-anisotropy for the free layer, a resistance-change can be detected, as shown in FIG. 1C and FIG. 1D, for the case that the free layer 40 has a perpendicular-anisotropy with either the compressive or tensile strain. Therefore, the strain sensor element and the pressure sensor element, being highly-sensitive and robust, can be realized. Thus, a strain can be detected if the free layer with the perpendicular-anisotropy is used for any case of the tensile strain and the compressive strain. This detection can not be realized if the free layer having the in-plane-anisotropy for prior art is used.

Thus the reason that a magnetic layer with the perpendicular-anisotropy is used in the MRAM and the STO is different to the reason for using it in the strain sensor element.

In the case of the MRAM it is necessary to use the perpendicular-anisotropy both for the free layer and the reference layer. This is because there is eventually a problem of the demagnetization field in the cases where the reference layer has the in-plane-anisotropy. It may be a potential issue for the realization of high-density memory cells. On the other hand, for the strain sensor of the invention, the in-plane-anisotropy can be used for the reference layer. Only for the free layer is it necessary to use the perpendicular-anisotropy.

In addition to this, there is also a difference in the structure because for the strain sensor element the reason for having the free layer with the perpendicular-anisotropy is different from the reason in the case of MRAM or the like. This detail is explained below.

In the case of the MRAM, a bit is written by a magnetic field or by a spin injection current. For both cases, it is necessary to realize the free layer having good-soft magnetic properties because it is necessary not to accidentally change the direction of the magnetization by other undesired means. Concretely, it is necessary to decrease the magnetostriction coefficient of a magnetic layer. This is also same as in the case of the STO. Change of the magnetization of the free layer by the compressive strain and the tensile strain will affect the operation of the STO. Therefore it is desirable to decrease the magnetostriction coefficient of the free layer. Specifically, it is desirable that the absolute value of the magnetostrictive coefficient is smaller than $10^{-6}$ both for the MRAM and the STO in general. There is also a restriction in the absolute value of the magnetostrictive coefficient of the read-head of a HDD, and the absolute value of the magnetostriction coefficient is required to be smaller than $10^{-6}$. For all of the existing application, small magnetostriction coefficient is needed to avoid the effects from an uncontrolled strain.

On the other hand, in the case of the strain sensor element and the pressure sensor element, it is desirable that there is a larger absolute value of the magnetostriction coefficient than with the MRAM and the STO in order to realize a changing of the direction of magnetization by the applied external stress. The magnetostrictive coefficient is explained below. By the balance of magnetic elasticity energy and magnetostatic energy, the formula related to the magnetostriction coefficient is described below.

$$(1/2)\Delta H_k B_s = (3/2)\Delta\sigma\lambda \quad (1)$$

$\Delta H_k$ indicates a change of magnetization of the free layer with the external strain, $B_s$ indicates a saturated magnetization, and $\Delta\sigma$ indicates a stress, $\lambda$ indicates the magnetostriction coefficient. From this formula, it is found that the magnetostriction coefficient $\lambda$ is needed to be larger in order to change $\Delta H_k$ greatly for a given value of $\Delta\sigma$. This notion is clearly opposite to the cases of HDD, MRAM, or the STO or like. As mentioned before, the absolute value of the magnetostriction coefficient $\lambda$ is preferred to be smaller than $10^{-6}$ in the cases of the read-head sensor of the HDD, MRAM, and STO. On the other hand, the small absolute value is not applicable to the detection for the external strain. This is because the small absolute value is not sufficient to generate a large enough energy change for the inverse-magnetostriction effect to be able to significantly change the direction of the magnetization of the free layer. Thus, when considering the strain sensor element, such as the embodiment of the invention, the small absolute value can not make the strain sensor element work because the small absolute value can not generate the necessary inverse-magnetostriction effect.

Another feature is that a material with the perpendicular-anisotropy has a magnetic anisotropy which is larger than that of a soft magnetic material with the in-plane-anisotropy. This is because it is hard for the perpendicular-anisotropy to overcome a shape anisotropy which favors the in-plane-anisotropy. By using a large magnetic anisotropy material, which means using a large $H_k$ material, the $\Delta H_k$ also needs to be large in order to detect a $\Delta H_k/H_k$. Thus, as understood from the formula (1), it is preferred that a larger magnetostrictive coefficient $\lambda$ of the free layer needs to be used than the case of using a magnetic material with the in-plane-anisotropy. It is preferred that the absolute value of the magnetostriction coefficient $\lambda$ of the strain sensor element to be larger than $10^{-6}$ or equal to $10^{-6}$.

The deposition sequence of the spin-valve film is the reference layer 20/the spacer layer 30/the free layer 40 (this structure is called "bottom type"); alternatively the free layer 40/the spacer layer 30/the reference layer 20 (this structure is called "top type" as the reference layer 20 is above the free layer 40) can be used to form the spin-valve film. The effect on the embodiment of the invention is substantially same between the two cases of the bottom type and the top type though FIG. 1A and FIG. 1B show the embodiment of the bottom type.

The under-layer 70 can be used for the cases of the bottom type with the reference layer 20/the spacer layer 30/the free layer 40 or the top type with the free layer 40/the spacer layer 30/the reference layer 20. In this specification the word "Under-layer" comprises broad concepts. "Under-layer" comprises a multilayer such as a buffer layer, a seed layer, or a pinning layer, or similar (not shown in the figures). Some of these layers can be omitted, depending on the film structure. The buffer layer is used for avoiding unexpected effects, such as the roughness generated from a flexible substrate. In the case where a coating layer 150 provides a buffer effect, the buffer layer can be omitted. The seed layer is used for controlling crystalline orientation of the reference layer 20/the spacer layer 30/the free layer 40 or the free layer 40/the spacer layer 30/the reference layer 20. The pinning layer can be used for pinning the magnetization of the reference layer if it is necessary for the magnetization of the reference layer to be pinned.

A spin-valve film 50 (the spin-valve film 50 is also denoted as the MR element 50) comprises the reference layer 20, the spacer layer 30, and the free layer 40. An electrode can be provided on the spin-valve film 50 because it is necessary for the spin-valve film 50 to have a sense current passed through the spin-valve film 50 in order to detect a resistance-change generated from the external stress.

More details of the spin-valve film 50 and the electrodes are shown in FIG. 1A and FIG. 1B.

In FIG. 1A the spin-valve film 50 is a CIP spin-valve (current passes through the plane of the spin-valve film), and the spin-valve film 50 comprises a pair of electrodes 501, 502 provided on the side of the spin-valve film 50. The coating layer 150 is used between the spin-valve film 50 and the substrate 15 to avoid current leakage from the spin-valve film 50 to the substrate 15. In FIG. 1A and FIG. 1B, the coating layer 150 has insulating properties.

A hard magnetic bias (hard magnetic material) is used for the electrodes 501, 502 to realize a single domain of the free layer 40.

In FIG. 1B the spin-valve film 50 is comprised of a CPP spin-valve (current passes perpendicularly to the plane of the spin-valve film) such as used in a CPP-GMR or a TMR spin-valve. A lower electrode 511 and an upper electrode 512 are used for supplying current to the spin-valve film 50. The coating layer 150 is used between the spin-valve film 50 and the substrate 15 to avoid the current leakage from the spin-valve film 50 to the substrate 15. In the case of the CPP spin-valve, an insulating film 600 is provided on the side of the spin-valve film 50.

By using lithographic processes, the electronic contact between the under electrode 511 and the substrate 15 is formed in the same manner as the electronic contact between the upper electrode 512 and the substrate 15. These details are omitted because these contacts can be formed by using prior arts.

The hard magnetic material is used for forming the single domain of the free layer 40 on the one side of the insulating film 600.

As shown in FIG. 1A and FIG. 1B, electrode locations are different between the CIP spin-valve and the CPP spin-valve, but the operating principle is basically same. Therefore, the electrodes are omitted from the following figures.

First Embodiment

The first embodiment of the invention is shown by using a spin-valve film in FIG. 1B. Si can be used for a substrate 15. In the case where the substrate 15 comprises Si, a membrane structure is formed by thinning the part of the substrate 15. The membrane structure is almost same as in the embodiment in FIG. 1A, and the spin-valve film is deposited on a thinned part of the substrate 15. However, materials other than Si can be used for the thinned part of the substrate 15 provided that it is possible to form the part of the substrate 15 which can be bended by the external strain.

For example, a flexible substrate can be used for the substrate 15, as mentioned below.

The substrate 15 is flexible or freely flexible film sheet. The substrate 15 can be made of materials which can bend. The substrate 15 is also made of a polymer material. For example, acrylonitrile butadiene styrene, cyclo-olefin polymer, ethylene-propylene-based rubber, polyamide, polyamide-imide, polybenzimidazole, polybutylene terephthalate, polycarbonate, polyethyne, polyetheretherketone, polyetherimide or possible, polyethylenimine, polyethylene naphthalate, polyester or polysulfone, polyethylene terephthalate, Phenol formaldehyde resin, polyimide, poly (methyl methacrylate), polymethylpentene, polyoxymethylene, polypropylene, m-phenyl ether, poly(p-phenylene sulfide), para-aramid, polystyrene, polysulphone, polyvinyl chloride, poly(tetrafluoroethene), perfluoroalkoxy, fluorinated ethylene propylene, poly(tetrafluoroethene), polyethylenetetrafluoroethylene, polyethylenechlorotrifluoroethylene, polyvinylidene fluoride, melamine formaldehyde, liquid-crystal polymers, or urea-formaldehyde can be used for the polymer material.

A coating layer 150 can be comprised of an organic material, such as poly (methyl methacrylate) or poly (p-phenylene sulfide) or inorganic material such as $Al_2O_3$ or $SiO_2$. The thickness of the coating layer 150 is about 10 nm or thicker in the case of an inorganic material. In the case of the organic material, the thickness of the coating layer 150 is several μm or more which depends on deposition condition.

The coating layer 150 has several purposes. One of them is to reduce the roughness of the surface of the substrate 15. This can improve the MR ratio and increase sensitivity. This can improve reliability and the manufacturing yield of a strain sensor element 10.

If the coating layer 150 has insulating properties, the coating layer 150 can help avoid current leakage from an electrode 511 to the substrate 15. The coating layer 150 modifies the transducer effect from the substrate 15 to the strain sensor element 10. The insulator coating layer 150 can improve sensitivity. If the coating layer 150 is made to be conductive then it can replace electrode 511 and thus simplify the structure of the strain sensor element 10.

The electrode 511, 512 are comprised of a metal with high conductivity. Cu, Au, or Ag are used for the electrode 511, 512. The electrode 511, 512 also can be made of magnetic material such as Co, Ni, or Fe.

An insulating film 600 has insulating properties in order to avoid current leakage from the strain sensor element 10. The insulating film 600 can be made of $Al_2O_3$ or $SiO_2$.

An under-layer 70 comprises a buffer layer, a seed layer, and a pinning layer. In this embodiment, the under-layer 70 can be made of Ta 3 nm/Ru 2 nm/IrMn 7 nm/CoFe 3 nm/Ru 0.9 nm. Ta is the buffer layer, Ru is the seed layer, and IrMn/CoFe/Ru is the pinning layer. When a magnetic layer is deposited on the seed layer made of Ru, the seed layer acts as a synthetic pinning layer. If the effect of the roughness of the substrate 15 is reduced by using the coating layer 150, the buffer layer can be omitted. The seed layer is used to improve crystalline properties. The pinning layer is used for pinning the magnetization of magnetic layer adjacent to the pinning layer.

A reference layer 20 comprises CoFe 2 nm/CoFeB 1 nm, and the reference layer 20 has an in-plane-anisotropy by the pinning layer.

A spacer layer 30 comprises MgO 2 nm. The thickness of the spacer layer 30 is determined by the dependency on RA (resistance area product).

In order to work as the strain sensor element 10, the MR ratio should large enough, and the magnetostrictive coefficient should also be large enough, as described previously. The required properties of the spin-valve layer are similar to that of the read-head of a HDD, MRAM and STO, but the last requirement of the magnetostriction coefficient is completely opposite to in those other cases.

As mentioned before, a free layer 40 has the perpendicular-anisotropy. As an example for the free layer 40 with the perpendicular-anisotropy, the free layer 40 can be made of CoFeB 1 nm/TbFe 3 nm. As known already, the MR ratio can be improved by using CoFeB on the interface between a magnetic layer and MgO. But an additional layer with the perpendicular-anisotropy can be used because it is hard to form the perpendicular-anisotropy by using only a single layer of CoFeB.

For this purpose a TbFe layer is used. If the Tb composition of the TbFe layer comprises no less than 20 atomic % or no more than 40 atomic %, then the TbFe layer will show the perpendicular anisotropy. A CoFe layer can be used between the CoFeB layer and the TbFe layer. The merit of the TbFe layer is that the magnetostriction coefficient is very large and positive. The absolute value of the magnetostriction coefficient is about $10^{-4}$. Using this large magnetostriction coefficient, it is easy to make the total of the magnetostriction coefficient of the free layer 40 to be greater than or equal to $10^{-6}$.

In the case of the TbFe layer, it is possible for the TbFe layer to be used for two purposes. The first is forming the free layer with perpendicular-anisotropy and the second is obtaining a large magnetostrictive coefficient. TbFe is a base material for the free layer 40 but additional elements can be added in the free layer 40.

For realizing the perpendicular-anisotropy, the other material can be used for the free layer 40. Another example is that the free layer 40 is made of CoFeB 1 nm/(Co 1 nm/Ni 1 nm)×n (n>=2). Co/Ni multilayer has the perpendicular-anisotropy. The thickness of the Co layer and the Ni layer should range from 0.5 nm to 2 nm. In order to work as the strain sensor element 10, the magnitude of the magnetostrictive coefficient of the free layer 40 should be greater than or equal to $10^{-6}$. An additional element such as FeSiB, which has the large magnetostrictive coefficient, can be used to enhance the magnetostrictive coefficient. The free layer 40 shows a positive large magnetostriction coefficient as whole the free layer 40 composed of multi magnetic layer because FeSiB shows the positive large magnetostriction coefficient, which is about $10^{-4}$. In this example, the film structure of the free layer 40 is CoFeB 1 nm/(Co 1 nm/Ni 1 nm)×n/FeSiB 2 nm.

As described in an example, the basic structure of the free layer 40 is comprised of a Mp layer and an Ml layer, where the Mp layer comprises a magnetic material with the perpendicular-anisotropy, and the Ml layer comprises a magnetic material with the large magnetostrictive coefficient, and the absolute value of the magnetostrictive coefficient is larger than $10^{-4}$. The multilayer of Mp/Ml, Ml/Mp, Mp/x/ Ml, Ml/x/Mp, x/Ml/Mp, Ml/Mp/x, x/Mp/Ml or Mp/Ml/x can be used, where an additional layer x is included as necessary. For example, the CoFeB layer and the CoFe layer can be used as layer x at the interface of the spacer layer 30 in order to enhance the MR ratio.

FePt, CoPt, CoPtPt, CoPtPt—$SiO_2$ granular, Co/Pd multilayer, Co/Pt multilayer or Co/Ir multilayer can be used for the Mp layer. The TbFe layer and the Co/Ni multilayer also can be used for the Mp layer as described above. The Mp layer thickness can be from 2 mono-layers to 10 mono-layers.

Ni, Ni alloy (large content of Ni such as $Ni_{95}Fe_5$), SmFe, DyFe, magnetic oxide material which contains Co, Fe, or Ni can be used for examples of the Ml layer. The TbFe layer and the FeSiB layer also can be used for the Ml layer as described above. As mentioned before, an amorphous alloy layer which is based on FeSiB can be used for Ml. Ni, Ni rich alloy, and SmFe show a large negative magnetostrictive coefficient. Therefore the direction of the magnetization will be opposite to that of a positive magnetostriction material. In this case, the sign of the magnetostriction of whole of the free layer 40 works as negative. An oxide of a magnetic material comprising Fe, Co, and Ni such as $CoOx$ (0<x<80), $FeOx$ (0<x<80), or $NiOx$ (0<x<80) shows the large positive magnetostriction coefficient. In this case the sign of the magnetostriction coefficient of whole the free layer 40 can be positive.

The function of Mp layer is to form the perpendicular-anisotropy. The CoFeB layer, which forms layer x, can be used in the interface of the spacer layer 30. The CoFeB layer also can work as the Mp layer when the thickness is thin. In this case, the perpendicular-anisotropy can be generated if the thickness of the CoFeB layer is thinner than 1 nm.

FIG. 1C and FIG. 1D show the operation of the strain sensor element 10. The broken arrow shows the direction of the magnetization of the reference layer 20. The solid arrow shows the direction of the magnetization of the free layer 40.

FIG. 1C and FIG. 1D demonstrate a state when the external stress is applied to the substrate 15. In this state, the external stress causes a strain which rotates the magnetization of the free layer 40 so that the magnetization of the free layer 40 undergoes a change in the component of the perpendicular angle between the free layer 40 and reference layer 20.

FIG. 1C shows the case that the external stress is small. FIG. 1D shows the case that the external stress is large. As these figures demonstrate, the stronger the external stress is, the larger the strain and thus the larger the degree of the rotation undergone by the magnetization of the free layer 40. Thus, the angle between the magnetization of the reference layer 20 and the magnetization of the free layer 40 differs depending on the magnitude of the external stress. Thus, the magnitude of the external stress can be detected because the magnitude of resistance will vary depending on the magnitude of the resulting strain. The direction of the magnetization of the free layer 40 can return to an initial state if the external stress is removed. This is a reversible change where the magnetization of the free layer 40 returns to the initial orientation due to the perpendicular-anisotropy.

The case is explained that the free layer 40 has the in-plane-anisotropy.

FIG. 2A shows a complimentary example where the strain sensor element 10 is located on the membrane structure. The strain sensor element 10 comprises the free layer 40 with the in-plane-anisotropy. In this case, a pressure sensor element comprises the membrane structure or the substrate 15 transferring pressure to the strain sensor element 10. FIG. 2A shows the cases where the strain sensor element 10 is located at three different positions (a), (b), and (c). FIG. 2A shows the free layer 40 which is a component of the strain sensor element 10. The solid arrows show the direction of the strain. The broken arrows show the direction of the magnetization of the free layer 40. The position (a) indicates the centre of the substrate 15. The positions (b) and (c) indicate the edge of the substrate 15.

The free layer 40 is assumed to have the positive magnetizative coefficient so that the magnetization of the free layer 40 can align towards the direction of the strain.

In the case of the position (b), the magnetization of the free layer 40 is expected to rotate towards the direction of the strain when the external stress is applied to the substrate 15. Therefore a magnetoresistance-change can be detected. On the other hand, in the case of the position (a) and (c), the magnetization of the free layer 40 can not rotate because the direction of the magnetization of the free layer 40 is already along the direction of the external strain. Therefore the external strain can not be detected because the magnetoresistance-change is not generated by applying the external strain. This is not preferable as SNR because an area which can detect the external strain is restricted.

FIG. 2B shows the cases where the strain sensor element 10 is located at three different positions (d), (e), and (f) on the substrate 15. Here, the pressure sensor element comprises the membrane structure or the substrate 15 transferring the stress to the strain sensor element 10. FIG. 2B shows the free layer 40 which is a component of the strain sensor element 10. The solid arrows show the direction of the resultant strain. The broken arrows show the direction of the magnetization of the free layer 40. The position (d) indicates the centre of the substrate 15. The position (e) and (f) indicate the edge of the substrate 15.

At the positions (d), (e), and (f) the external strain is perpendicular to the direction of the magnetization of the free layer 40. The free layer 40 is assumed to have the positive magnetostrictive coefficient so that the magnetization of the free layer 40 can favour aligning towards the direction of the external strain.

In the case of positions (d), (e), and (f), the resultant strain can rotate in the direction of the magnetization of the free layer 40. In the case of position (d), the magnetization of the free layer 40 also rotates without the direction of the magnetization being well defined. Thus, the strain sensor element 10 can be used to detect the external strain anywhere of the membrane structure. This is opposite to the case shown in FIG. 2A. Thus, this embodiment can be used to enhance the SNR of the strain sensor element 10. This reason is that the free layer 40 has the perpendicular-anisotropy.

First Modified Example

FIG. 3 shows the first modified example of a strain sensor element 10. The strain sensor element 10 differs from the first embodiment by the presence of two ferromagnetic layers 60, 75. The ferromagnetic layer 60, 75 are positioned adjacent to a reference layer 20 on a substrate 15.

The field of the ferromagnetic layer 60, 75 forces the alignment of the magnetisation of the reference layer 20, causing it to be pinned. The ferromagnetic layer 60, 75 can be made of a transition metal element such as Fe, Co and Ni. CoPt, CoPtCr, or FePt alloy or the alloys based on them also can be used for the ferromagnetic layer 60, 75. Alloys with other elements thereof or made of rare-earth elements and alloys thereof, such as Sm—Co or Nd—Fe—Bo can be used for the ferromagnetic layer 60, 75.

Second Modified Example

FIG. 4 shows the second modified example of a strain sensor element 10. The second modified example of the strain sensor element 10 differs from the first embodiment by the presence of a ferromagnetic layer 80 and a non-magnetic layer 90 which are positioned between a reference layer 20 and a substrate 15. The ferromagnetic layer 80 is provided on the substrate 15. The non-magnetic layer 90 is provided on the ferromagnetic layer 80.

The ferromagnetic layer 80 is used to pin the magnetization of the reference layer 20. The ferromagnetic layer 80 has a greater magnetic anisotropy than that of the reference layer 20. The ferromagnetic layer 80 is made of a Co—Pt alloy.

Third Modified Example

FIG. 5 shows the third modified example of a strain sensor element 10. The third modified example of the strain sensor element 10 differs from the first embodiment by the presence of an antiferromagnetic layer 100, an ferromagnetic layer 110, and a non-magnetic layer 120. The antiferromagnetic layer 100 is provided on the substrate 15. The ferromagnetic layer 110 is provided on the antiferromagnetic layer 100. The non-magnetic layer 120 is provided on the ferromagnetic layer 110. This structure causes a synthetic antiferromagnet (SAF).

The antiferromagnetic layer 100 is made of a material containing IrMn or PtMn. Preferable thicknesses of the antiferromagnetic layer 100 are between 5 nm and 20 nm.

The ferromagnetic layer 110 is made of a CoFe alloy.

The non-magnetic layer 120 is made of Ru. The thickness of the non-magnetic layer 120 is no less than 0.5 nm and no more than 2 nm.

The advantage of using the SAF is that the stray field from the SAF is low, thus undesirable effects can be reduced.

Fourth Modified Example

FIG. 6 shows the fourth modified example of a strain sensor element 10. The fourth modified example of the strain sensor element 10 differs from the first embodiment by having an anisotropic shape. The anisotropic shape of a MR element 50 becomes extended along a specific direction. This structure forces the direction of the magnetization of a reference layer 20 in the longitudinal direction of the MR element 50.

As the anisotropy in the shape becomes greater, the magnetization of the reference layer 20 can easily turn to the longitudinal direction. This effect can be used to pin the magnetization in-plane or perpendicular by using a high aspect ratio. This anisotropically shaped structure can be used in addition to the above designs to customize magnetization free energy.

Fifth Modified Example

FIG. 7 shows the fifth modified example of a strain sensor element 10. The fifth modified example of the strain sensor element 10 differs from the first embodiment by the presence of two ferromagnetic layers 130, 140. The ferromagnetic layer 130 is provided on the reference layer 20. The ferromagnetic layer 140 is provided on the spacer layer 30. In this modified example a spacer layer 30 is MgO, thus the strain sensor element 10 utilizes resistance change from TMR effect.

The ferromagnetic layers 130 and 140 have an in-plane-anisotropy.

The ferromagnetic layers 130 and 140 are made of a CoFeB alloy. The thickness of the ferromagnetic layers 130 and 140 are no less than 3 nm and no more than 10 nm.

Second Embodiment

FIG. 8 shows a strain sensor element device 200 using an array of strain sensor element 10. The strain sensor elements 10 are regularly aligned on a substrate 15. The separation between each strain sensor element 10 can be determined by a design. For example, from several tens of nm to several mm can be designed. The merit of small separation is that it can be used to enhance the output signal for better SNR. On the other hand, too many devices may result in much wiring and so have large power consumption. As long as the total number of devices is sufficient for detecting pressure, a large separation is preferred for consumer use at a reasonable price.

However, this can be made larger or smaller depending on the size of the strain sensor element 10 and the area of coverage and the degree of sensitivity needed for any particular application of the strain sensor element device 200.

Each strain sensor element 10 is electrically connected to a control unit 210 by a pair of wires, aligned in intersecting directions, known as a word-line 220 and a bit-line 230. By choosing a specific word-line 220 and bit-line 230, a unique strain sensor element 10 can be addressed by the control unit 210. This enables the external strain of the substrate 15 to be measured at many points concurrently in order to determine the localized strain of the substrate 15. The strain sensor element device 200 takes advantage of the design of these strain sensor elements 10 where they are sensitive to in-plane strains from any direction.

FIG. 9 shows the structure of the electrode and wires used to connect the strain sensor element device 200.

The electrodes are made of a high conductivity material. These electrodes are made of a material with Au, Cu, or Al. Each strain sensor element 10 has a top electrode and a bottom electrode which is connected to a wire which forms the word-lines 220 and the bit-lines 230.

The direction of the word-lines 220 and bit-lines 230 are such that they intersect each other and can cross at each strain sensor element 10. The word-lines 220 and the bit-lines 230 connect each strain sensor element 10 to the next adjacent one.

FIG. 10 shows the strain sensor element device 200 in a preferred position. The strain sensor element device 200 uses a single strain sensor element 10 provided on the substrate 15. The substrate 15 is a flexible $SiO_2$ membrane fabricated from $SiO_2$/Si substrate. In this design the substrate 15 is circular in plan view, although square or rectangle shapes are permissible as required by to fabrication considerations.

The strain sensor element 10 is provided between an electrode 260 and an electrode 270. The electrode 270 is provided on the substrate 15. The electrode 260 is provided on the strain sensor element 10. If the substrate 15 is made of a flexible conductive film, such as doped polymer poly (3,4-ethylenedioxythiophene)poly(styrenesulfonate), the electrode 270 does not need to be connected to the strain sensor element 10 directly. Reducing the amount of wiring can make the film more flexible.

The strain sensor element 10 is positioned in the centre of the substrate 15, where the isotropic strain created by the substrate 15 is greatest. The strain sensor element device 200 takes advantage of the ability for this design of the strain sensor element 10 to respond to the isotropic strain.

FIG. 11A shows the structure of the electrodes in the substrate 15. The substrate 15 is comprised of a rigid substrate 16 and a membrane 17. The membrane 17 is fixed on the rigid substrate 16. A conductive film 240 is provided on the membrane 17. The conductive film 240 can be in addition to a priming layer 150, or a conductive priming layer can be used. The strain sensor element 10 is provided on the conductive film 240. The strain sensor element 10 is surrounded with an insulating layer 250. The top of the strain sensor element 10 is connected with an electrode 260.

The thickness of the electrode 260 is at least 100 nm so as to ensure good electrical connections, although thinner electrode 260 is possible given high quality deposition.

The insulating layer 250 is made of a material with $SiO_2$, or $Si_3N_4$. The insulating layer 250 also can use an organic material such as poly(methyl methacrylate) or insulating undoped Poly(3,4-ethylenedioxythiophene)poly(styrenesulfonate).

The electrode 260 can be made of a conductive film. The electrode 260 has the advantage of helping the membrane 17 to flex more easily and help make the strain more uniform, although it also can result in making the electrical contacting with the strain sensor element 10 more complicated.

FIG. 11B and FIG. 11C show the operation of the strain sensor element 10. The solid arrow shows the direction of the magnetization of the free layer 40 and the broken arrow shows the direction of the magnetization of the reference layer 20 (individual layers not indicated).

FIG. 11B and FIG. 11C show the state when the external stress is applied to the substrate 16, which is provided under the membrane 17. In this state, the external stress causes a strain which can rotate the magnetization of the free layer 40 so that the magnetization of the free layer 40 undergoes a change in the component of the perpendicular angle between the free layer 40 and reference layer 20.

Because the substrate 16 is inflexible when the external stress is applied, no strain occurs in this part of the substrate 16. The membrane 17 is flexible, so the strain can occur in this free-standing region where it is not bonded to the substrate 16. Because the shape of the membrane 17 is well defined, the strain resulting from an applied stress is consistent. The strain sensor element 10 is positioned on the membrane 17 in the most advantageous position for the strain that will be induced.

FIG. 11B shows the case that the external stress is small. FIG. 11C shows the case that the external stress is large. As these figures show, the stronger the stress and resultant strain is, the larger the degree of the rotation of the magnetization of the free layer 40 undergoes.

When the external stress is applied to the strain sensor element 10, the magnetization of the free layer 40 can rotate towards the axis of the strain. This rotation creates an angle between the magnetisation of the reference layer 20 and the free layer 40. When the strain sensor element 10 is no longer under the external stress, there will be no strain and the direction of the magnetisation of the free layer 40 can return to the initial state.

FIG. 12 shows the structure of the electrodes on the substrate 16. The strain sensor element 10 is provided between an electrode 270 and the electrode 260. The electrode 260 is provided on the top of the strain sensor element 10 and the membrane 17 without intersecting to electrode 270.

A further dielectric layer can be deposited above the electrodes in order to insulate it from external influences.

FIG. 13 shows the strain sensor element device 200 using multiple strain sensor elements 10 on a substrate 15.

The strain sensor elements 10 are provided on the substrate 15 in a square pattern and are electrically connected to form a Wheatstone bridge style arrangement. The voltage across the strain sensor element 10 is read out from the terminals in the middle of the square, as per Wheatstone bridge operation. Because multiple strain sensor elements 10 can be provided on the substrate 15, this and other measurement bridge circuits can be used.

FIG. 14 shows the strain sensor element device 200 using a plurality of strain sensor elements 10 on the substrate 15.

The strain sensor elements 10 are connected in a serial arrangement. This is done in order to increase the strength of the signal and average the output by including the data from many strain sensor elements 10. This structure takes advantage of the ability for the strain sensor elements 10 to operate in a variety of locations on the substrate 15 without being sensitive to the direction of the anisotropic strain, thus making it feasible to include many strain sensor elements 10. Other alternative circuit arrangements can be used, depending on the required functionality, such as individually wiring each strain sensor element 10 so it can be addressed separately by control units and then processing the results in the control unit or other connected processing/output system.

Third Embodiment

FIG. 15 shows an apparatus 300 which applies the strain sensor element 10.

The apparatus 300 indicates a blood pressure sensor. The upper figure of FIG. 15 shows the state when an artery does not expand with blood. The lower figure of FIG. 15 shows the state the artery is expanded by the blood pressure.

The apparatus 300 is wrapped around a wrist or other body position where there is an artery close to the surface, and is used to measure heart rate.

When the heart beats the artery expands with blood, which is known as a pulse. The stress from the artery applies a force to a substrate 15, and this causes a strain. This strain is detected by a strain sensor element 10 provided on the substrate 15, and the resulting change in magnetoresistance is electrically recorded by control units measuring the strain sensor elements 10. Electrical signals showing the extent of the expansion of the artery and the occurrence frequency are interpreted from the measured data by a computer, allowing the heart rate and blood pressure to be determined.

FIG. 16 shows an apparatus 400 which applies the strain sensor element 10.

The apparatus 400 indicates a switch device. The upper figure of FIG. 16 shows the state where a button is not pressed. The lower figure of FIG. 16 shows the state when the button is pressed.

This apparatus 400 is for a common switch, such as on a remote control. A button 410 is provided on the rigid substrate 16 featuring a membrane 17. The button 410 is made of rubber.

When the button 410 is pressed, a pressure is transferred to the membrane 17 which distorts due to the stress. In this case, the strain sensor element 10 is provided on the underside of the membrane 17, where it and the related wiring can be less prone to damage from impact with the button. This position also ensures that the strain sensor element 10 can undergo a tensile strain rather than a compressive strain.

While certain embodiments of the invention have been described, these embodiments have been presented by way of example only, and are not intended to limit the scope of the embodiment of the inventions. Indeed, the novel elements and apparatuses described herein can be embodied in a variety of other forms; furthermore, various omissions, substitutions and changes in the form of the methods and systems described herein can be made without departing from the spirit of the embodiment of the invention. The accompanying claims and their equivalents are intended to cover such forms or modifications as would fall within the scope and spirit of the embodiment of the invention.

What is claimed is:

1. A strain sensor element comprising:
a laminated film provided above a substrate,
the laminated film comprising:
   a free layer which has a perpendicular magnetic anisotropy, wherein the free layer has a first magnetization;
   a reference layer comprising a second magnetization; and
   a spacer layer provided between the free layer and the reference layer; and
a pair of electrodes configured to cause a current to flow through the laminated film,
wherein a rotation angle of the first magnetization of the free layer in response to a distortion of the substrate is different from a rotation angle of the second magnetization of the reference layer in response to the distortion of the substrate.

2. The element according to claim 1,
wherein the free layer comprises a ferromagnetic material, and
wherein an absolute value of a magnetostriction coefficient of the free layer is larger than $10^{-6}$.

3. The element according to claim 1,
wherein the free layer comprises an Mp layer and an Ml layer, and
wherein the Mp layer comprises a magnetic material which shows perpendicular magnetic anisotropy, and the Ml layer comprises a magnetic material which shows an absolute value of a magnetistriction coefficient of larger than $10^{-4}$.

4. The element according to claim 3,
wherein the Mp layer comprises at least one of:
a TbFe layer,
a (Co/Ni) multilayer,
a (Co/Pd) multilayer,
a (Co/Pt) multilayer,
a (Co/Ir) multilayer,
a FePt layer,
a CoPt layer,
a CoPt—$SiO_2$ granular layer, or
a CoFeB layer which is thinner than 1 nm.

5. The element according to claim 3,
wherein the Ml layer comprises at least one of:
TbFe,
SmFe,
DyFe,
FeSiB,
FeOx (0<x<80),
CoOx (0<x<80),
NiOx (0<x<80), or
Ni.

6. The element according to claim 1,
wherein the free layer further comprises a layer of CoFeB or CoFe at an interface with the spacer layer.

7. The element according to claim 1,
wherein the one of the pair of electrodes, the reference layer, the spacer layer, and the free layer are arranged on the substrate in this order.

8. The element according to claim 1, further comprising:
first and second ferromagnetic layers which sandwich the reference layer therebetween.

9. The element according to claim 1, further comprising:
a non-magnetic layer, a ferromagnetic layer, and an antiferromagnetic layer disposed between the reference layer and the substrate, the non-magnetic layer being disposed adjacent to the reference layer, the antiferromagnetic layer being disposed adjacent to the substrate, the ferromagnetic layer being sandwiched between the non-magnetic layer and the antiferromagnetic layer.

10. The element according to claim 1,
wherein the laminated film is elongated in one direction.

11. The element according to claim 1, further comprising:
a first ferromagnetic layer disposed between the free layer and the spacer layer; and a second ferromagnetic layer disposed between the spacer layer and the reference layer.

12. The element according to claim 1,
wherein the substrate has
a circular shape,
a square shape, or
a rectangle shape.

13. The element according to claim 1, further comprising:
a button provided on the other one of the pair of electrodes.

14. The element according to claim 1,
wherein the substrate comprises Si, and
wherein a part of the substrate is made thinner compared with an other part to thereby function as a membrane.

15. The element according to claim 1,
wherein the substrate is made of polymer material.

16. The element according to claim 1,
wherein the strain sensor element comprising a plurality of strain sensor elements, each strain sensor element comprising the laminated film.

17. A blood pressure sensor comprising:
a strain sensor element comprising:
a laminated film provided above a substrate,
the laminated film comprising:
   a free layer which has a perpendicular magnetic anisotropy, wherein the free layer has a first magnetization;
   a reference layer comprising a second magnetization;
   a spacer layer provided between the free layer and the reference layer; and
a pair of electrodes configured to cause a current to flow through the laminated film,
wherein a rotation angle of the first magnetization of the free layer in response to a distortion of the substrate is different from a rotation angle of the second magnetization of the reference layer in response to the distortion of the substrate.

18. The sensor according to claim 17,
wherein the free layer further comprises an Ml layer, and
wherein the Ml layer comprises a magnetic material which shows an absolute value of a magnetistriction coefficient of larger than $10^{-4}$.

19. The sensor according to claim 18,
wherein the Ml layer comprises at least one of:
TbFe,
SmFe,
DyFe,
FeSiB,
FeOx (0<x<80),
CoOx (0<x<80),
NiOx (0<x<80), and
Ni.

20. A strain sensor element comprising:
a laminated film provided above a substrate,
the laminated film comprising:
- a free layer which comprises an Mp layer, wherein the free layer has a first magnetization;
- a reference layer comprising a second magnetization;
- a spacer layer provided between the free layer and the reference layer; and
a pair of electrodes configured to cause a current to flow through the laminated film,
wherein a rotation angle of the first magnetization of the free layer in response to a distortion of the substrate is different from a rotation angle of the second magnetization of the reference layer in response to the distortion of the substrate,
wherein the Mp layer comprises at least one of:
a TbFe layer,
a (Co/Ni) multilayer,
a (Co/Pd) multilayer,
a (Co/Pt) multilayer,
a (Co/Ir) multilayer,
a FePt layer,
a CoPt layer,
a CoPt—$SiO_2$ granular layer, or
a CoFeB layer which is thinner than 1 nm.

21. A blood pressure sensor comprising:
a strain sensor element comprising:
a laminated film provided above a substrate,
the laminated film comprising:
- a free layer which comprises an Mp layer, wherein the free layer has a first magnetization;
- a reference layer comprising a second magnetization;
- a spacer layer provided between the free layer and the reference layer; and
a pair of electrodes configured to cause a current to flow through the laminated film,
wherein a rotation angle of the first magnetization of the free layer in response to a distortion of the substrate is different from a rotation angle of the second magnetization of the reference layer in response to the distortion of the substrate,
wherein the Mp layer comprises at least one of:
a TbFe layer,
a (Co/Ni) multilayer,
a (Co/Pd) multilayer,
a (Co/Pt) multilayer,
a (Co/Ir) multilayer,
a FePt layer,
a CoPt layer,
a CoPt—$SiO_2$ granular layer, or
a CoFeB layer which is thinner than 1 nm.

* * * * *